United States Patent [19]

Hollinger et al.

[11] Patent Number: 4,515,274
[45] Date of Patent: May 7, 1985

[54] PARTICLE ANALYZING AND SORTING APPARATUS

[75] Inventors: John D. Hollinger; Raul I. Pedroso, both of Miami, Fla.

[73] Assignee: Coulter Corporation, Hialeah, Fla.

[21] Appl. No.: 326,734

[22] Filed: Dec. 2, 1981

[51] Int. Cl.³ .............................................. B07C 5/02
[52] U.S. Cl. ..................................... 209/3.1; 209/571;
209/906; 356/39; 356/73; 356/246
[58] Field of Search ........................... 209/3.1–3.3,
209/571, 579, 906, 127 R, 577, 555, 556;
356/72, 73, 39, 335, 246; 250/222.1, 222.2;
361/226; 346/75; 324/71 CP, 71.4

[56] References Cited

U.S. PATENT DOCUMENTS

| 2,656,508 | 10/1953 | Coulter | 324/71 |
| 3,710,933 | 1/1973 | Fulwyler et al. | 209/3 |
| 3,871,770 | 3/1975 | von Behrens et al. | 250/222.2 |
| 3,873,204 | 3/1975 | Friedman et al. | 356/39 |
| 4,014,611 | 3/1977 | Simpson et al. | 324/71.4 |
| 4,348,107 | 9/1982 | Leif | 356/72 |
| 4,395,676 | 7/1983 | Hollinger et al. | 324/71.4 |

OTHER PUBLICATIONS

E. Menke, E. Kordwig, P. Stuhlmuller, V. Kachel and G. Ruhenstroth-Bauer; "A Volume-Activated Cell Sorter", *The Journal of Histochemistry and Cytochemistry*; vol. 25, No. 7, pp. 796–803, 1977.

R. A. Thomas, T. A. Yopp, B. D. Watson, D. H. K. Hindman, B. F. Cameron, S. B. Leif, R. C. Leif, L. Roque and W. Britt; "Combined Optical and Electronic Analysis of Cells with the AMAC Transducers", *The Journal of Histochemistry and Cytochemistry*; vol. 25, No. 7, pp. 827–835, 1977.

*Primary Examiner*—Robert B. Reeves
*Assistant Examiner*—Donald T. Hajec
*Attorney, Agent, or Firm*—Gerald R. Hibnick

[57] ABSTRACT

Disclosed is a flow-through, particle analyzer and sorter apparatus for simultaneous optical and electrical impedance measurements on a stream of particles, comprising a flow cell having a pair of channels fluidly connected by a particle sensing aperture, through which the particles pass and are analyzed; a nozzle mounted at the end of the downstream channel so as to define a flow chamber; a sheath liquid which is introduced at the bottom of the flow chamber to hydrodynamically focus the particle stream and to jet the same in a liquid jet from the nozzle; and a system for creating droplets from the liquid jet and for thereafter sorting the droplets.

8 Claims, 2 Drawing Figures

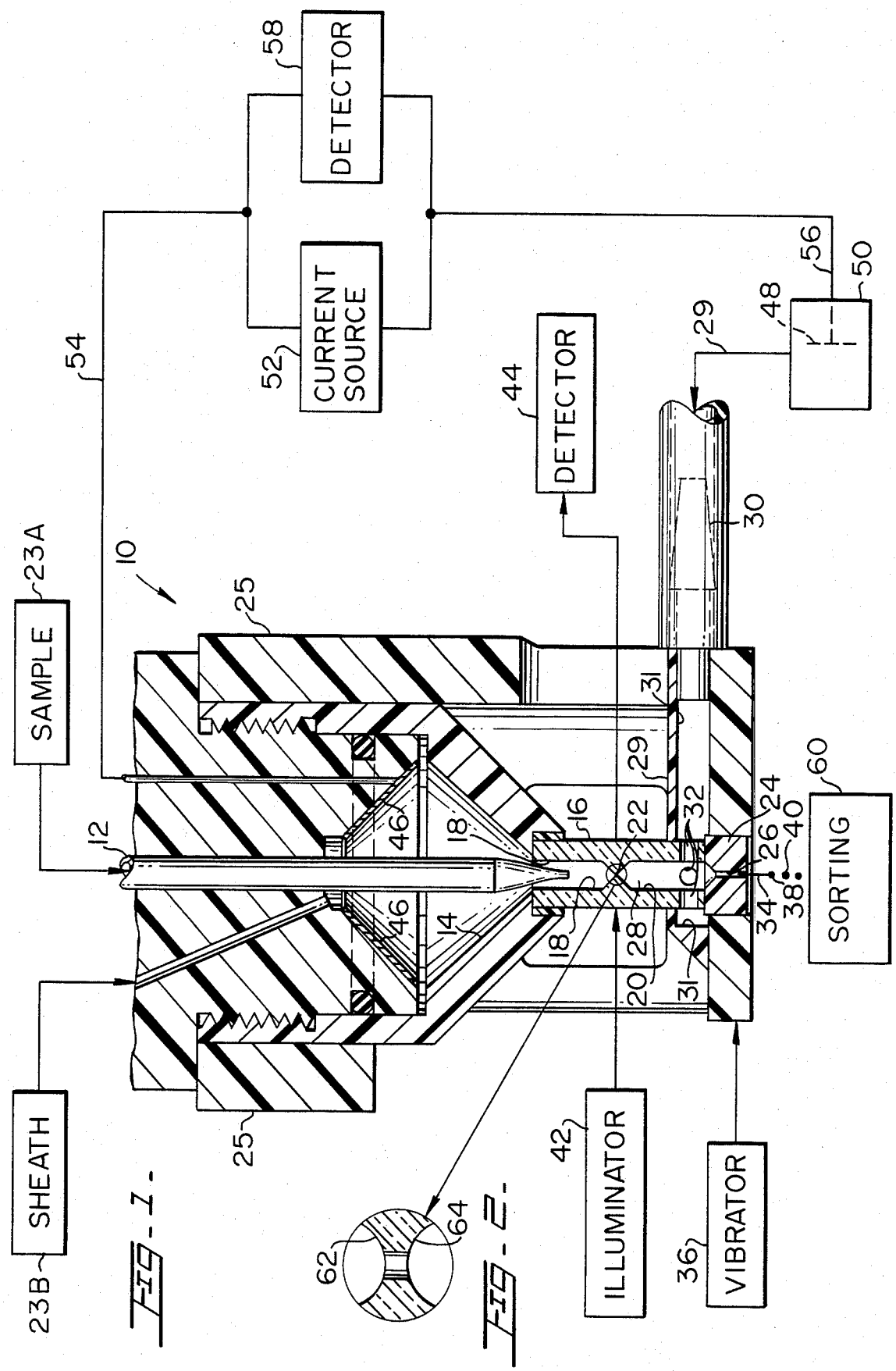

PARTICLE ANALYZING AND SORTING APPARATUS

BACKGROUND OF THE INVENTION

1. Field of the Invention

The invention relates generally to particle analyzing and sorting apparatus and more particularly is concerned with apparatuses in which studies may be made of particulate systems using the impedance sensing principle and optical measurements.

2. Description of Prior Art

Since its conception in the early 1950's, the principle of particle counting and sizing invented by Wallace H. Coulter has resulted in numerous methods and flow-through apparatuses for the electronic counting, sizing and analysis of microscopic particles, which are scanned in a fluid suspension, as shown by the pioneer U.S. Pat. No. 2,656,508 to Coulter. In this prior art arrangement, a D.C. electric current flow is established between two vessels by suspending electrodes in the respective bodies of the suspension fluid. The only fluid connection between the two bodies is through an orifice; hence, an electric current flow and field are established in the orifice. The orifice and the resultant electric field in and around it constitute a sensing zone. As each particle passes through the sensing zone, for the duration of the passage, the impedance of the contents of the sensing zone will change, thereby modulating the current flow and electric field in the sensing zone, and causing the generation of a signal to be applied to a detector suitably arranged to respond to such change. (The mark "Coulter" is a registered trademark, Registration No. 995,825, of Coultier Electronics, Inc. of Hialeah, Fla.).

For many applications of automated, flow-through particle analyzers, it is not possible to use just a small number of particle descriptors for identification of each type of cell present in a heterodisperse cell population of a sample. At present, many flow systems measure fluorescence, light scattering and electronic cell volume (impedance sensing). Additionally, there have evolved flow-through particle analyzers wherein the particles are positioned inside of liquid droplets and the droplets are sorted upon the above described measurements. Such sorting particle analyzers are shown in U.S. Pat. No. 3,710,933 to Fulwyler et al. and in an article entitled "A Volume-Activated Cell Sorter", *The Joiurnal of Histochemistry and Cytochemistry*, by E. Menke et al., Vol. 25, pp. 796–803, 1977.

Major design problems are brought about by the use of both optical measurements and impedance measurements in the storing particle analyzers. The above described sorting particle analyzers of the prior art perform electronic cell volume measurements prior to the optical measurements, making it necessary to correlate the two types of measurements. This correlation problem is not significant at very low particle flow rates; however, at high particle flow rates, it is possible for the detected signals to be scrambled by such artifacts as aggregates of cells which pull apart after they traverse a volume-sensing orifice, so as to move separately to the optical sensing zone, the presence of nonfluorescing particles; and the possibility of two neighboring cells exchanging position in the flow stream. Additionally, this requires the use of special circuitry for compensating for the time delay between the optical and electronic signals for a given particle.

Where sorting is not used, there has been developed a combined electro-optical particle analyzer in which all measurements are made simultaneously, thereby eliminating the complexity and uncertainty of correlating data obtained from sequential measurements. This electro-optical particle analyzer is described in an article entitled "Combined Optical and Electronic Analysis of Cells with AMAC Transducers", by Thomas et al., published in *The Journal of Histochemistry and Cytochemistry*, Vol. 25, No. 7, (1977), pp. 827–835. This multiparameter particle analyzer uses a square sensing orifice wherein all parameters are measured simultaneously. The square orifice is enclosed inside a cube formed by adhering four pyramids together.

U.S. Pat. Nos. 3,710,933 to Fulwyler et al., 3,502,974 to Coulter et al. and 3,502,973 to Coulter et al. and the above mentioned article to Thomas et al. are incorporated by specific reference thereto.

SUMMARY OF INVENTION

The present invention is directed toward a combined electro-optical partical analyzing and sorting apparatus, wherein both optical and electrical impedance (electronic volume) measurements are simultaneously made on a stream of particles passing through a particle sensing aperture. The flow cell has a pair of channels, an upstream channel and a downstream channel, defining openings at opposed ends thereof, with the particle sensing aperture fluidly connecting the two channels. The improvement in the apparatus comprises mounting a nozzle, containing an exit orifice, at the end of the downstream channel, so as to define a liquid-filled flow chamber. A sheath liquid is provided at the lower end of the flow chamber to provide a sheath for the particle stream over the entire length of the small diameter flow chamber, thereby leaving room in the flow cell, adjacent to the upper end of the downstream channel, for illuminating the particles and collecting light therefrom. By virtue of this design, the stream of particles are hydrodynamically focused as they proceed to the exit orifice and thereafter become part of a liquid jet. The liquid jet, in a conventional manner, is broken into a plurality of droplets, which are charged and sorted, based upon the above-described signals.

Heretofore, droplet sorting had never been included in an electro-optical apparatus wherein electrical impedance and optical measurements are made simultaneously. Moreover, the applicants found that despite the small volume of the flow chamber, hydrodynamic focusing of the stream of particles by a liquid sheath could be accomplished by introducing the sheath liquid in the bottom of the downstream orifice and thereby not interfering with the optical assembly.

DESCRIPTION OF DRAWINGS

Further objects and advantages of the present invention will become apparent as the following description proceeds, taken in conjunction with the accompanying drawing in which:

FIG. 1 illustrates a part cross-sectioned view and part block diagram of a particle analyzing and sorting apparatus according to the invention; and FIG. 2 is an enlarged cross-sectional view of the sensing aperture region of the flow cell of FIG. 1.

DESCRIPTION OF THE PREFERRED EMBODIMENT

FIG. 1 illustrates a flow through, particle analyzing and sorting apparatus 10 having a sample introduction tube 12, a sheath tube 14 positioned in surrounding, coaxial relationship to the tube 12, and an optically transparent flow cell 16 positioned at the end of the tube 12. The flow cell 16 has formed therein a pair of opposed bores or channels 18 and 20 and a microscopic sensing aperture 22, which forms a fluid passageway between the ends of the channels. The aperture 22 defines a particle sensing zone to be described hereinafter. A liquid stream of individually suspended particles, originally from a pressurized reservoir (23A), proceeds through the tube 12. A saline laminar liquid sheath, originally from another pressurized reservoir (23B), proceeds through the tube 14 so as to surround the stream of particles. As the liquid stream of particles exits from the tube 12, and enters the first channel 18, hydrodynamic pressures reduce the diameter of the stream of particles as the stream obtains the velocity of the liquid sheath. The liquid sheath also acts to center the stream of particles so that particles pass through the orifice 22. After leaving the orifice 22, the paticles enter the second channel 20, of the flow cell 16.

Various system components are supported by a cylindrical frame 25. A nozzle 24, with an exit orifice 26 formed therein, is mounted to the end of the flow cell 16, so that the nozzle 24 and second channel 20 define a liquid-filled flow chamber 28. A tube 29 is coupled to the frame 25 by a conduit fitting 30. A second sheath liquid is fed via the tube 29 to a liquid cavity 31, which is in fluid communication with three inlet orifices 32 formed in the wall of the flow cell 16. Due to the pressure drop associated with the aperture 22, it is necessary to introduce the second sheath liquid into the flow chamber 28 to create a second sheath having sufficient hydrodynamic pressures to pass the particles through the flow chamber 28 and out the exit orifice 26.

Contrary to the prior art designs, the second liquid sheath is introduced at the lower portion of the flow chamber 28, resulting in advantages in optical illumination and collection, which will be described hereinafter. More specifically, the sheath liquid enters the second channel 20 through the plurality of inlet orifice 32 positioned at locations a considerable distance below and downstream of the sensing aperture 22. Moreover, the second sheath liquid is introduced in a non-concentric manner relative to the particle stream exiting from the sensing aperture 22 and is injected into a relatively small interior volume of the second channel 20. Despite the small volume of the second channel 20 and the non-concentric introduction of the second liquid sheath at the bottom of the second channel 20, it has been found that a portion of the second sheath liquid travels "uphill" to capture the particle stream exiting from the sensing aperture 22, while a portion of the second sheath liquid goes immediately to the exit orifice 26 and all points in-between. In this manner, good hydrodynamic focusing of the particle stream through the flow chamber 28 is accomplished, thereby allowing the stream to exit from the exit orifice 26. In the preferred embodiment, three inlet orifices 32 are shown. However, it should be understood that the number of orifices 21 are a mere matter of design choice, and one will suffice, although, depending upon their diameter, it is convenient to have more than one, so as to allow for cleaning and flushing of the flow chamber 28.

The system components shown schematically in block form are those which exist normaly in conventional particle analyzer and sorting systems, sometimes referred to as flow cytometric sorting systems. Only those components of the particle analyzer and sorter 10 have been shown which are necessary to explain the operation of the present invention.

In a conventional manner, vibratory energy is applied to the liquid jet 34, exiting from the exit orifice 26, by vibratory means 36. As one possibility, the vibratory means 36 can comprise a piezo-electric crystal. The flow cell 16 is mounted to and supported by a piezo-electric crystal which vibrates the flow cell 16 at a high frequency. The exact frequency at which the cell 16 vibrates is dependent on the selected diameter of the exit orifice 26. These vibrations impart small disturbances, normally undulations, on the surface of the jet 34 which grow, due to well known surface tension effects, and eventually pinch the jet off at a breakoff point 38 into well defined droplets 40. The diameter of the exit orifice 26, the velocity of the liquid jet 34 and the dilution of the particle suspension are all predetermined so that normally there is no more than one cell in a given droplet 40.

By means of a conventional sorting arrangement 60, the selected droplets 40 are charged by, for example, a charging collar having a voltage applied thereto. Other droplets are not charged. The sorting arrangement 60 also includes a pair of deflector plates having an electrical potential difference applied therebetween. As the droplets pass between the plates, the charged droplets are deflected in the electric field, thereby allowing the charged droplets to be separated from the uncharged droplets. The decision to charge a given droplet is based upon the previously described optical and impedance measurements for the particle contained within that droplet. The above description of the droplet forming and droplet sorting is only briefly given, since this portion of the apparatus 10 is well known in the art.

In the flow cell 16 the particle suspension is illuminated in a conventional manner, while passing through the sensing aperture 22, by a light beam provided by an illumination source 42 (normally a laser). The response of the particle in the sample suspension to the illumination (normally light scatter, fluorescence, or absorbance) is detected by an optical detector system 44. As is well known in the art, there are numerous illumination and light collection arrangements which can be used with the flow cell 16. However, by positioning the inlet orifice 32 substantially downstream of the aperture 22 according to the invention, the orifices 32 do not interfere with light illumination and collection; hence, greater solid angles of light illumination and collection are possible.

The sensing aperture 22 not only serves as an optical sensing zone as described above, but also serves as an electronic volume sensing zone, according to the principle of Wallace Coulter, as will be described below. An upstream electrode 46 is preferably mounted interiorly to the sheath tube 14. A downstream electrode 48 is preferably mounted in a remote chamber 50, which is in fluid communication with the flow chamber 28 through the tube 29. A low frequency current (including D.C.) or high frequency current source 52 or both is electrically coupled to the electrodes 46 and 48 by way of electrical conductors 54 and 46 respectively. As the particles pass through the aperture 22, they modulate the electrical current so as to produce particle pulses detected by conventional detector circuitry 58. Illustrative current source 52 and detection circuitry 58 are shown in incorporated U.S. Pat. Nos. 3,710,933; 3,502,974 and 3,502,973.

Preferably, but not necessarily, the channels 18 and 20 have a circular cross section of 0.05 inches with the overall length of the flow cell being 0.25 inches. The flow cell 16 is formed from a monolithic piece of quartz, which allows for the flow cell 16 to be quite small. The smaller the size of the flow cell 16, the better its optical characteristics, in that the flow cell approaches a point source for the optical signals. The cross section of the particle sensing aperture 22 preferably approximates a square. As seen in the further enlargement of FIG. 2, the ends of the channels 18 and 20 are formed with spherical surfaces 62 and 64, which are each interrupted by the aperture 22. By providing rounded ends for the bores, the aperture 22 does not have to be precisely located. The outside surfaces are flat and parallel to the walls of the aperture 22. Typically, the aperture 22 has walls with lengths of 50 to 100 micrometers. Preferably, the aperture 22, the exit orifice 26 and the channels 18 and 20 are coaxially aligned. The above-described dimensions and configurations described in this paragraph are merely illustrative and can assume other shapes and sizes, respectively.

Although the apparatus is used primarily for studying cells, it is equally applicable to other kinds of particles.

Although particular embodiments of the invention have been shown and described herein, there is no intention thereby to limit the invention to the details of such embodiments. On the contrary, the intention is to cover all modifications, alternatives, embodiments, usages and equivalents of the subject invention as fall within the spirit and scope of the invention, specification and the appended claims.

What is claimed is:

1. A particle analyzing and sorting apparatus for studying particles in suspension, said apparatus including a flow cell having a particle sensing aperture through which a stream of said particles in suspension is passed, means for passing an electric current through said sensing aperture simultaneously with passage of a particle through said sensing aperture, first detecting means responsive to electrical impedance variations for generating a particle pulse signal with the passage of said particle through said aperture, illumination means for providing radiation to illuminate said particle in said particle sensing aperture, second detecting means responsive to optical effects caused by the passage of said particle through said radiation for generating an analog electrical signal, said flow cell having an upstream channel and a downstream channel formed in opposed ends of said flow cell, said particle sensing aperture being disposed in fluid connecting relationship between said channels, said apparatus being further characterized by:
   a nozzle, including an exit orifice, mounted at the end of said flow cell adjacent said downstream channel so that said downstream channel and said nozzle defines a flow chamber;
   means for introducing a sheath liquid into said flow chamber, proximate said exit orifice and proximate to the downstream end of the downstream channel, to hydronamically focus said stream of particles as said stream proceeds from said particle sensing aperture to said exit orifice and for jetting said stream in a liquid jet from said nozzle;
   means for periodically disturbing said liquid jet to produce droplets containing said particles; and
   means for sorting said droplets based on said signals.

2. The particle analyzing and sorting apparatus according to claim 1, wherein said flow chamber has a lower end adjacent said nozzle and a remote from said particle sensing orifice and wherein said means for introducing said sheath liquid includes means for introducing said sheath liquid in said lower portion of said flow chamber, whereby said introducing of said sheath liquid does not interfere with said radiation and does not interfere with said optical effects.

3. The particle analyzing and sorting apparatus according to claim 2, wherein said means for introducing said sheath liquid in the lower portion of said flow chamber includes at least one inlet orifice formed in said flow cell to provide liquid communication with the lower portion of said downstream channel.

4. A particle analyzing and sorting apparatus for studying particles in suspension, said apparatus including a flow cell having a particle sensing aperture through which a stream of said particles in suspension is passed, means for passing an electric current through said sensing aperture simultaneously with passage of a particle through said sensing aperture, first detecting means responsive to electrical impedance variations for generating a particle pulse signal with the passage of said particle through said aperture, illumination means for providing radiation to illuminate said particle in said particle sensing aperture, second detecting means responsive to optical effects caused by the passage of said particle through said radiation for generating an analog electrical signal, said flow cell having an upstream channel and a downstream channel formed in opposed ends of said flow cell, said particle sensing aperture being disposed in fluid connecting relationship between said channels, wherein said channels are formed with rounded ends and said particle sensing aperture opens into said rounded ends, whereby positioning of said particle sensing aperture relative to said channels becomes less critical, said apparatus being further characterized by:
   a nozzle, including an exit orifice, mounted at the end of said flow cell adjacent said downstream channel so that said downstream channel and said nozzle defines a flow chamber;
   means for introducing a sheath liquid into said flow chamber, proximate said exit orifice and proximate to the downstream end of the downstream channel, to hydronamically focus said stream of particles as said stream proceeds from said particle sensing aperture to said exit orifice and for jetting said stream in a liquid jet from said nozzle;
   means for periodically disturbing said liquid jet to produce droplets containing said particles; and
   means for sorting said droplets based on said signals.

5. A particle analyzing apparatus for studying particles in suspension, said apparatus including a flow cell having a particle sensing aperture through which a stream of particles in suspension is passed, said flow cell having an upstream channel and a downstream channel, with said particle sensing aperture being positioned therebetween and being the only fluid connection between said channels, said downstream channel having a downstream end, which is the end remote from said particle sensing orifice, exit means positioned proximate the downstream end of said downstream channel, sheath liquid introducing means constructed and positioned proximate to said exit means and proximate to the downstream end of said downstream channel and operating for introducing sheath liquid which flows both into said exit means as well as toward the upstream positioned particle sensing means aperture for hydrodynamically focusing the stream of particles as it flows downstream from said particle sensing aperture into said exit means.

6. A particle analyzing apparatus according to claim 5 in which said sheath liquid introducing means is constructed and arranged with respect to the stream of particles so as to introduce the sheath liquid in a non-concentric manner.

7. A particle analyzing apparatus according to claim 5 and further including: illumination means for providing radiation to illuminate particles in said particle sensing aperture, said illumination means and its radiation being oriented and positioned substantially remote from said sheath liquid introducing means; said exit means including a nozzle having an exit orifice for jetting the stream of particles as a liquid jet from said nozzle; and disturbing means for periodically disturbing the liquid jet to produce droplets containing particles.

8. A particle analyzing apparatus for studying particles in suspension, said apparatus including a flow cell having a particle sensing aperture through which a stream of particles in suspension is passed, said flow cell having an upstream channel and a downstream channel, with said particle sensing aperture being positioned therebetween and being the only fluid connection between said channels, said downstream channel having a downstream end, which is the end remote from said particle sensing orifice, exit means positioned proximate the downstream end of said downstream channel, sheath liquid introducing means constructed and positioned proximate to said exit means and proximate to the downstream end of said downstream channel and operating for introducing sheath liquid which flows both into said exit means as well as toward the upstream positioned particle sensing aperture for hydrodynamically focusing the stream of particles as it flows downstream from said particle sensing aperture into said exit means, and in which said sheath liquid introducing means is constructed and arranged with respect to the stream of particles such that the sheath liquid enters said flow cell to meet at approximately right angles the stream of particles.

* * * * *

UNITED STATES PATENT AND TRADEMARK OFFICE
CERTIFICATE OF CORRECTION

PATENT NO. : 4,515,274
DATED : May 7, 1985
INVENTOR(S) : John David Hollinger et al.

It is certified that error appears in the above—identified patent and that said Letters Patent is hereby corrected as shown below:

Column 1, line 35, change "Coultier" to --Coulter--;
         line 50, change "Joiurnal" to --Journal--;
         line 55, change "storing" to --sorting--.
Column 3, line 66, change "21" to --32--.
Column 4, line 68, change "46" to --56--.
Column 5, line 9, change "cell" to --cell 16--.
Column 6, line 8, after "and" delete --a--;
         line 53, after "from" change "aid" to --said--.

Signed and Sealed this

Eighth Day of October 1985

[SEAL]

Attest:

DONALD J. QUIGG

Attesting Officer

Commissioner of Patents and
Trademarks—Designate